United States Patent
Miller et al.

(10) Patent No.: US 10,603,019 B2
(45) Date of Patent: Mar. 31, 2020

(54) ADHESIVE APPLICATOR

(71) Applicant: ADVANCED MEDICAL SOLUTIONS LIMITED, Cheshire (GB)

(72) Inventors: Guy Stephen Miller, Saltash (GB); Simon Mark Parish, Exeter (GB)

(73) Assignee: ADVANCED MEDICAL SOLUTIONS LIMITED, Cheshire (GB)

( * ) Notice: Subject to any disclaimer, the term of this patent is extended or adjusted under 35 U.S.C. 154(b) by 156 days.

(21) Appl. No.: 15/540,655

(22) PCT Filed: Dec. 22, 2015

(86) PCT No.: PCT/GB2015/054119
§ 371 (c)(1),
(2) Date: Jun. 29, 2017

(87) PCT Pub. No.: WO2016/108042
PCT Pub. Date: Jul. 7, 2016

(65) Prior Publication Data
US 2017/0354406 A1 Dec. 14, 2017

(30) Foreign Application Priority Data
Dec. 29, 2014 (GB) .................................. 1423306.8

(51) Int. Cl.
*A61B 17/08* (2006.01)
*A61B 17/00* (2006.01)
(Continued)

(52) U.S. Cl.
CPC .... *A61B 17/00491* (2013.01); *A61L 24/0015* (2013.01); *A61L 24/046* (2013.01);
(Continued)

(58) Field of Classification Search
CPC .......... A61B 17/0057; A61B 17/00491; A61B 17/005; A61B 2017/0042;
(Continued)

(56) References Cited

U.S. PATENT DOCUMENTS

| 2,784,127 A | 3/1957 | Joyner et al. |
| 3,527,224 A | 9/1970 | Rabinowitz |

(Continued)

FOREIGN PATENT DOCUMENTS

| GB | 2462136 | 2/2010 |
| GB | 2462136 A | 2/2010 |

(Continued)

OTHER PUBLICATIONS

International Search Report for PCT/GB2015/054119 dated Mar. 29, 2016, 4 pages.
(Continued)

*Primary Examiner* — Vi X Nguyen
(74) *Attorney, Agent, or Firm* — Nixon & Vanderhye P.C.

(57) ABSTRACT

An adhesive applicator includes a receiver having a tubular body with a closed first end and an opposed second end, the tubular body having a deformable wall, an adhesive composition contained within the tubular body, and an applicator tip mounted on the tubular body and comprising a foam material having an applicator external of the applicator for applying the adhesive, the applicator being such that deformation of the tubular body causes the adhesive to be expressed through the applicator tip. The foam material is a reticulated foam felt and allows for relatively constant flow of the adhesive through the foam felt and to the applicator surface thereof over a wide range of viscosity conditions of the adhesive and pressure applied to the deformable body of the applicator.

16 Claims, 4 Drawing Sheets

(51) Int. Cl.
*A61L 24/00* (2006.01)
*A61L 24/04* (2006.01)
*B05C 17/005* (2006.01)
*B05C 17/00* (2006.01)

(52) U.S. Cl.
CPC .... *B05C 17/005* (2013.01); *A61B 2017/0042* (2013.01); *A61L 2300/404* (2013.01); *B05C 17/002* (2013.01)

(58) Field of Classification Search
CPC .......... A61B 2017/00637; A61B 17/08; A61B 2017/0057; A61B 2017/085
See application file for complete search history.

(56) References Cited

U.S. PATENT DOCUMENTS

| | | |
|---|---|---|
| 3,591,676 A | 7/1971 | Hawkins et al. |
| 3,667,472 A | 6/1972 | Halpern |
| 3,995,641 A | 12/1976 | Kronenthal et al. |
| 4,035,334 A | 7/1977 | Davydov et al. |
| 4,444,933 A | 4/1984 | Columbus et al. |
| 4,650,826 A | 3/1987 | Waniczek et al. |
| 4,906,317 A | 3/1990 | Liu |
| 5,288,159 A | 2/1994 | Wirt |
| 5,480,935 A | 1/1996 | Greff et al. |
| 5,762,919 A | 6/1998 | Greff et al. |
| 5,791,801 A | 8/1998 | Miller |
| 5,962,010 A | 10/1999 | Greff et al. |
| 6,439,789 B1 | 8/2002 | Ballance et al. |
| 6,475,331 B1 | 11/2002 | O'Connor et al. |
| 6,595,940 B1 * | 7/2003 | D'Alessio ........... A61M 35/003 401/132 |
| 6,729,786 B1 | 5/2004 | Tufts et al. |
| 6,835,789 B1 | 12/2004 | Kneafsey et al. |
| 8,729,121 B2 | 5/2014 | Zhang et al. |
| 2003/0031499 A1 | 2/2003 | Heard et al. |
| 2004/0179889 A1 | 9/2004 | Tufts et al. |
| 2006/0072959 A1 | 4/2006 | Tufts et al. |
| 2008/0046004 A1 * | 2/2008 | Stenton ............ A61B 17/00491 606/214 |
| 2008/0298879 A1 | 12/2008 | Chesak et al. |

FOREIGN PATENT DOCUMENTS

| | | |
|---|---|---|
| JP | 1994-277297 A | 10/1994 |
| JP | 2006-520271 A | 9/2006 |
| JP | 2007-527256 A | 9/2007 |
| WO | WO 92/21448 | 12/1992 |
| WO | WO 00/38777 | 7/2000 |
| WO | WO 2003/000815 | 1/2003 |
| WO | WO2004/83905 | 9/2004 |
| WO | WO 2006/131747 | 12/2006 |
| WO | WO 2008/001067 | 1/2008 |
| WO | WO 2008/121827 | 10/2008 |

OTHER PUBLICATIONS

Written Opinion of the ISA for PCT/GB2015/054119 dated Mar. 29, 2016, 6 pages.
Great Britain Search Report dated May 27, 2015, issued in connection with Application No. GB1423306.8.
Office Action dated Sep. 24, 2019 issued in Japanese Application No. 2017-535820 (with translation).

* cited by examiner

ADHESIVE APPLICATOR

This application is the U.S. national phase of International Application No. PCT/GB2015/054119 filed Dec. 22, 2015 which designated the U.S. and claims priority to GB Patent Application No. 1423306.8 filed Dec. 29, 2014, the entire contents of each of which are hereby incorporated by reference.

The present invention relates to adhesive applicators. The invention relates more particularly, but not necessarily exclusively, to adhesive applicators useful for application of adhesives (e.g. polymerisable cyanoacrylate compositions) to wound and skin sites. The applicator has particular, but not sole, application to adhesive applicators for closure of incisions made during surgery and more generally for wound closure (e.g. cuts to the skin of a human or other animal patient) and also for skin protection applications (e.g. for application of an adhesive composition to prevent blister formation, to prevent skin maceration and for application to intact skin around a wound to prevent bacteria and/or other microorganisms potentially present on the skin from entering into the wound).

Minimally invasive surgery, such as laparoscopic surgery, is typically accomplished using small incisions. Such small incisions can be closed by traditional techniques, such as the introduction of sutures or staples to close the incision wounds. However, more recently the use of surgical adhesives has gained favor in closing incisions and wounds, with preferable surgical adhesive materials for this purpose being liquids containing cyanoacrylate moieties. Upon contact with surface proteins and moisture in skin or other body tissue, the cyanoacrylate polymerizes such that the resulting polymer bonds strongly to the skin.

Thus, when applied over apposed skin sections of a wound, the adhesive polymerises and joins these apposed skin sections to result in closure of the wound. Conveniently, the adhesive need not be removed from the wound because it will naturally fall away from the wound as the skin renews itself.

Many different applicators have been developed for application of cyanoacrylate adhesives to skin or tissue. Such applicators may comprise a sealed, frangible ampoule preloaded (by the manufacturer of the applicator) within a deformable body of the applicator whereby deformation of the body causes the ampoule to fracture and adhesive to be passed to and through an applicator tip of the applicator. Such an applicator is described in WO2008/001067. Alternatively, such applicators may comprise a deformable body containing the adhesive and closed by a removable plug located at an end of the body. Deformation of the body causes the plug to be moved towards the applicator tip to allow the adhesive composition to be released from within the body and be expressed through the applicator tip. Such an applicator is described in GB 2462136 A. Irrespective of the particular type of applicator, the tubular body may be provided with a pair of diametrically opposed wings which are squeezed together to cause release of the adhesive composition (e.g. by virtue of fracturing the ampoule or dislodging the plug) and expression of the adhesive composition through the applicator tip.

However, consistency of application of cyanoacrylate adhesives with such applicators is difficult, and this can affect the setting time of the adhesive being used. If the amount of adhesive applied is too thick, the setting time may be too long for effective use.

Thus, for example, a user of the applicator disclosed in WO2008/001067 or GB 2462136 A may find it difficult to gauge the force required to apply to the wings to dispense the adequate amount of adhesive. Moreover, different adhesives may be formulated with varying viscosity levels depending on the manufacturer. Octyl cyanoacrylates (e.g. 1-methylheptyl cyanoacrylate), for example, have a higher viscosity than do butyl cyanoacrylates. Cyanoacrylate formulations can also have their viscosities increased through the addition of rheology modifiers. As a result, a surgeon using applicators from different manufacturers may have difficulty determining the correct manner of application to achieve consistent adhesive thickness during application. Moreover, cyanoacrylate-based adhesives can auto-polymerise over time, causing an increase in viscosity as the adhesive ages. This further hinders consistency of application.

Similar difficulties are experienced in other wound closure and skin protection applications.

It is an object of the present invention to obviate or mitigate the abovementioned disadvantages.

According to the present invention there is provided an adhesive applicator comprising
- a receiver having a tubular body with a closed first end and an opposed second end, said tubular body having a deformable wall,
- an adhesive composition contained within the tubular body, and
- an applicator tip mounted on the tubular body and comprising a foam material having an applicator surface external of the applicator for applying said adhesive, the applicator being such that deformation of the tubular body causes said adhesive to be expressed through the applicator tip,
- wherein the foam material is a reticulated foam felt.

Thus, the applicator of the present invention has an applicator tip including a reticulated foam felt which is the means by which the adhesive is applied to a substrate. We have found that the use of a reticulated foam felt allows for relatively constant flow of the adhesive through the foam felt and to the applicator surface thereof over a much wider range of viscosity conditions of the adhesive and pressure applied to the deformable body of the applicator to fracture the ampoule and express adhesive through the foam felt. Thus, consistency of application is ensured.

The receiver is preferably of a synthetic plastics material.

The adhesive preferably comprises polymerisable cyanoacrylate moieties, as conventionally used in such applicators. The applicator has particular, but not sole application, in the case where the adhesive comprises an octyl cyanoacrylate (e.g. 1-methylheptyl cyanoacrylate (CAS 133978-15-1)).

The applicator of the present invention has particular utility in medical applications for the application of adhesive compositions to wound and skin sites, e.g. as outlined in the opening paragraph of the present specification.

The invention has particular application to applicators having wings which are squeezed together to deform the tubular body to release and express adhesive.

The applicator may be one in which the second end of the body is open and the adhesive is contained within a sealed ampoule formed of a frangible material such that deformation of the wall fractures the ampoule to release the adhesive composition contained therein and express the adhesive composition through the applicator tip. Thus, for example, the applicator may be of the same general type as disclosed in WO 2008/001067.

Alternatively, the applicator may be of the type in which a plug is located in the second end of the tubular body to retain the adhesive composition therein and the plug is moveable towards the applicator tip on deformation of the tubular body to allow adhesive to be released from the body and to be expressed through the applicator tip. This, for example, the applicator may be of the general type disclosed in GB 2462136 A.

Alternatively, the applicator may be of the type disclosed in WO 2006/131747.

The applicator of the present invention utilises a specific form of foam material, namely reticulated foam felt, which possess properties useful for adhesive application. The reticulated foam felt absorbs and transmits adhesive released from the ampoule, and is used to dispense adhesive onto a substrate surface directly.

Reticulated foam felts possess high void volumes, uniform porosity, high breathability and uniform texture. Reticulated foam felts also possess strong "wicking" properties: the foam is able to draw in liquids into its foam structure thereby enabling it to be utilised as a storage reservoir for liquids. It is these properties which make reticulated foam felts ideal for use in the applicators of the present invention. The foam felt used herein is able to wick-away liquid released from a fractured ampoule into its 3D foam structure as a reservoir of adhesive. Moreover, its uniform surface texture means that it can function as a consistent applicator to dispensing liquid adhesive stored within onto a substrate surface.

Reticulated foams are understood in the art to be a type of open-cell foam having a skeletal structure such that there are few (if any) closed cells within the foam or membranes between the cells. Thus the structure of a reticulated foam (as its name suggests) is a 3D reticulated network of 'filaments' meeting at vertices to form the skeletal structure.

Reticulated foam felts are produced by permanently compressing reticulated foams so that the 3D skeletal structure thereof forms a more densely packed network of open cells. Heat is typically used in order to "set" the structure and thereby to cause it to retain its shape after compression is released. Compression in this way causes the foam material to take on the aforementioned properties by increasing its density, reducing pore sizes and increasing foam firmness.

The reticulated foam felt material is preferably comprised of polyurethane, e.g. a polyether polyurethane or a polyester polyurethane. Polyurethane foams have good biocompatibility and are therefore particularly useful for medical applications.

The foam felt material preferably has a firmness grade (also known as "compression ratio") of at least about 2 although preferably not more than about 5. The compression ratio may be from about 2 to about 4, preferably about 3. The firmness grade/compression ratio is calculated by taking the thickness of the foam material before compression divided by the thickness of the material after compression. Preferably, the reticulated foam felt used in the applicator of the invention is produced by compression of a reticulated foam having 80 to 100 ppi (pores per linear inch), more preferably 85 to 95 ppi, e.g. about 90 ppi. Suitable foam felt materials for use in the present invention may be acquired from Foamex™ and are sold under the brandname "SIF Felt®".

Preferably the reticulated foam felt used in the applicator tip of the applicator of the invention has a thickness of 1 to 10 mm, e.g. about 3 mm.

It will be appreciated that the reticulated foam felt may be of any shape appropriate for application of adhesive to a substrate (e.g. skin or other tissue). It is, however, preferred that the applicator tip comprises a single piece of foam felt configured to provide two planar applicator surfaces at an acute angle to each other. This shape allows for fine and broad application dependant on orientation.

At least for the case where the applicator comprises a frangible ampoule containing the adhesive composition, the applicator preferably further comprises a shard barrier between the ampoule and the reticulated foam felt for inhibiting shards of the ampoule, once fractured, from contacting the foam felt material. The shard barrier is preferably in the form of a mesh. The apertures in the mesh preferably have dimensions such that they will not allow passage of a shard having a dimension greater than 0.5 mm. If the apertures of the mesh are square then each mesh aperture may have a side length of 0.35 mm. It will however be appreciated that other configurations are possible, e.g. circular holes with a diameter not greater than 0.5 mm, more preferably not greater than 0.35 mm. Such the apertures are able to block passage of shards which might be large enough to pass through the reticulated foam felt and cause injury.

The applicator tip preferably comprises a hollow former mounted on the open end of the tubular body and having an openwork end face remote from the body and inclined to the longitudinal axis thereof. In such an embodiment the openwork end face is configured as the mesh, and said reticulated foam felt is supported over the end face of the former.

In a preferred embodiment the former has first and second planar sides which are opposed to each other and which extend over different lengths away from the tubular body. In such an embodiment the former further comprises third and fourth planar sides that are opposed to each other, said foam felt material being located over said end face and at least partly over the first and second sides.

The first, second, third and fourth planar sides are preferably impermeable to adhesive.

The reticulated foam felt may be held in position by a collar locating around the base of the former. The collar has two opposed lugs projecting there from, each configured to locate over a respective one of the third and fourth planar sides of the former body, said third and fourth planar sides and said lugs having co-operating formations to locate the collar in position.

It will however be appreciated that other methods of fixing the foam in position may be adopted, e.g. sonic welding, heat welding, adhesive etc.

Each of the third and fourth sides may be provided with a raised formation formed with a ridge extending transverse to the axis of the tubular body, and each of said lugs may be formed on its inner surface with a recess complementary to said raised formation and formed with a groove complementary to said ridge.

The applicator may further comprise a pair of wings positioned diametrically across the tubular body, each wing being affixed at one end to the receiver, with the other end being splayed out away from the tubular wall but being movable toward the tubular wall when a user applies opposing finger pressure to the splayed ends so as to effect deformation of the wall of the body (e.g. to fracture an ampoule contained therein or dislodge a plug retaining the adhesive composition in the body). Each of the wings may have a pressure barb facing toward and bearing upon the tubular wall, through which a deforming force may be applied to the tubular wall upon movement of the wings.

The distance of pressure barbs and may be no less than 2 mm and no greater than 8 mm from the end of sealed ampoule.

Each of the wings may additionally comprise a pressure pad facing toward the tubular wall, through which pressure pad a compressing force may be applied to the tubular wall for expressing adhesive from the tubular body.

The adhesive composition may comprise a polymerisable cyanoacrylate ester adhesive which, in monomeric form, is represented formula I:

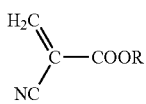

where R is selected from: alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula II:

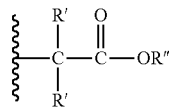

wherein each R' is independently selected from: hydrogen and methyl, and R" is selected from: alkyl of from 1 to 6 carbon atoms, alkenyl of from 2 to 6 carbon atoms, alkynyl of from 2 to 6 carbon atoms, cycloalkyl of from 3 to 8 carbon atoms, aralkyl selected from benzyl, methylbenzyl and phenylethyl, phenyl, and phenyl substituted with 1 to 3 substituents selected from hydroxy, chloro, bromo, nitro, of alkyl 1 to 4 carbon atoms, and alkoxy of from 1 to 4 carbon atoms.

It is to be understood that the term "polymerizable cyanoacrylate ester" refers to polymerizable formulations comprising cyanoacrylate monomers or polymerizable oligomers which, in their monomeric form, are preferably compounds represented by formula I as described above.

In situ polymerization of such cyanoacrylate compositions provides for an adherent polymeric film which acts to close and seal an incision or wound.

Since the polymeric film is naturally shed from the skin surface two to four days following application, there is no need to effect removal adhesive following surgery, therefore avoiding the skin trauma such as that associated with removal of surgical sutures or staples.

The polymerizable cyanoacrylate esters described herein rapidly polymerize in the presence of water vapor or tissue protein, and the n-butyl-cyanoacrylate bonds to mammalian skin tissue without causing histotoxicity or cytotoxicity. Polymerization occurs at ambient skin temperature while maintaining the skin surface under suitable conditions to allow polymerization to proceed. In general, the length of time required for polymerization will vary depending on factors such as the amount of adhesive composition applied, the temperature of the skin, the moisture content of the skin, the surface area of skin to which the adhesive was applied, and the like. However, polymerization is typically complete within about 10 to about 60 seconds, while the skin is maintained at ambient conditions.

Polymerizable cyanoacrylate esters are known in the art and are described in, for example, U.S. Pat. Nos. 3,527,224; 3,591,676; 3,667,472; 3,995,641; 4,035,334; and 4,650,826, the entire disclosures of which are incorporated herein by reference in their entirety.

The cyanoacrylate ester is preferably 1-methylheptyl cyanoacrylate.

In embodiments, the sealing-strengthening layer of liquid cyanoacrylate laid down by the applicator may have a thickness of no more that about 1 millimeter and yield a polymerized cyanoacrylate composition layer that has a thickness of no more than about 1 millimeter. The polymer layer and the liquid layer may have a uniform thickness of from about 2 to about 500 μm, such as from about 20 to about 100 μm.

The adhesive composition may include a curing accelerator, examples of which are disclosed in U.S. Pat. Nos. 8,729,121, 6,475,331, WO 2003/000815, U.S. Pat. Nos. 6,835,789, and 4,906,317.

The adhesive composition may include a rheology modifier, e.g. polymethyl methacrylate.

The adhesive composition may include an acidic stabiliser (e.g. sulphur dioxide) and/or a free radical stabiliser (e.g. butylated hydroxyanisole).

Optionally, the cyanoacrylate composition applied by the present applicator can include a "biocompatible plasticizer." As used herein, the term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933, the entire disclosures of which are incorporated herein by reference in their entirety. Specific plasticizers include, by way of example only, acetyl tri-n-butyl citrate, acetyl trihexyl citrate butyl benzyl phthalate, dibutyl phthalate, dioctylphthalate, n-butyryl tri-n-hexyl citrate, diethylene glycol dibenzoate and the like.

Optionally, the cyanoacrylate adhesive formulation can include therapeutic agents such as analgesics, anti-inflammatory agents, antimicrobial agents, and the like.

As used herein, the term "antimicrobial agent" refers to agents which destroy microbes (i.e., bacteria, fungi, yeasts, prions and viruses) thereby preventing their development and their pathogenic action. In preferred embodiments, the cyanoacrylate composition may contain from about 0.01 to about 5 weight-percent antimicrobial. The addition of antimicrobial agents to the cyanoacrylate composition results in the gradual release of the antimicrobial from the polymerized cyanoacrylate composition, providing antimicrobial at a level that provides protection for post-surgical infection.

Cyanoacrylate compositions useful in the practice of this invention are also disclosed in U.S. Pat. No. 5,480,935, the entire disclosure of which is incorporated herein by reference in its entirety. In an embodiment, the cyanoacrylate adhesive composition further comprises an antimicrobially effective amount of a compatible antimicrobial agent. Such compositions may comprise from about 0.1 to about 40, such as 1 to 30, or 5 to 20 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. Pat. No. 5,762,919, the entire disclosure of which is incorporated herein by reference in its entirety.

The biocompatible antimicrobial agent may comprise a complex of iodine molecules with a biocompatible polymer. Such complexes are well known in the art and the resulting complex typically comprises both available iodine and iodide anions. These complexes, on contact with mammalian skin, provide for a source of antimicrobial iodine. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, from about 5 to about 40 weight percent, such as from about 10 to about 25 weight percent, may be added to the cyanoacrylate composition based on the total weight of the composition.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The use of a compatible antimicrobial agent in the composition permits the agent to be released from the polymeric film thereby reducing microbial growth under the film.

Other medicaments suitable for use in conjunction with the cyanoacrylate composition include corticoid steroids such as described by Greff, et al. in U.S. Pat. No. 5,962,010 which is incorporated herein by reference in its entirety and analgesic compounds such as lidocaine. The former reduces inflammation at the site of the application whereas the latter reduces pain. Combinations of a steroid with an analgesic are also contemplated.

The adhesive may include other components, such as polymerisation initiators and/or accelerators.

The invention will now be further described, by way of example only, with reference to the accompanying drawings, in which.

Figure 1:
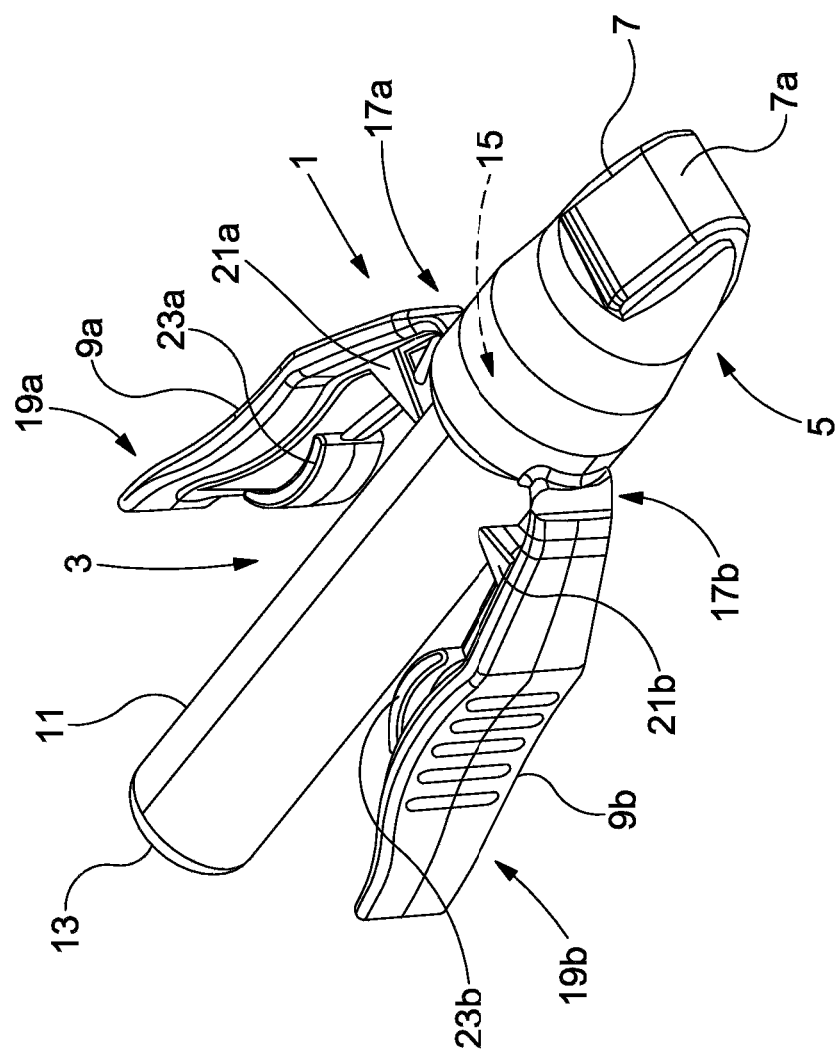
FIG. 1 is a schematic perspective view of one embodiment of adhesive applicator in accordance with the present invention.

The figures illustrate an applicator 1 in accordance with the present invention for applying an adhesive (such as a surgical adhesive to an incision) to a substrate surface. The applicator 1 depicted herein is a relatively small device, designed to be gripped with a user's fingers for careful adhesive application.

The applicator 1 includes a generally tubular receiver 3 accommodating a sealed ampoule of adhesive (not visible) and an applicator tip 5 mounted on one end of the receiver 3. The applicator tip 5 comprises a reticulated foam felt material 7 having applicator surfaces 7a-c external of the applicator 1 for applying adhesive from the ampoule to a substrate surface. The ampoule in the receiver 3 is formed of a material suitable for containing adhesive, but which is also frangible (i.e. breakable) in response to pressure applied to it through the receiver 3. The applicator 1 also includes a pair of wings 9a, 9b for assisting release of the adhesive by breaking the ampoule in the manner explained more fully below. As described more fully below, squeezing of the wings 9a and 9b relatively towards each other results in fracture of the ampoule and causes the adhesive released to be expressed through the applicator tip 5.

Figure 4:
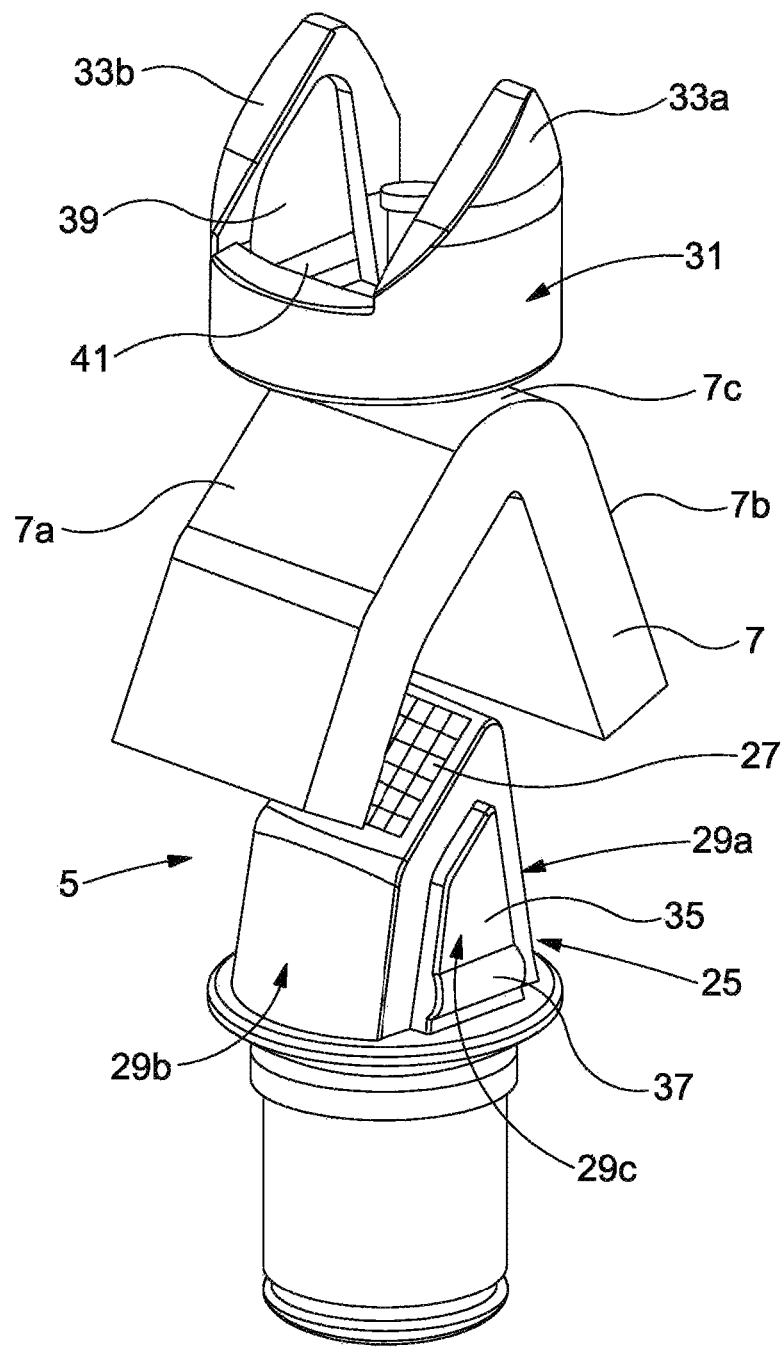
FIG. 4 is an exploded perspective view to an enlarged scale of the applicator tip of the adhesive applicator depicted in FIG. 1.

Reference is now made to FIG. 4, which shows the applicator tip 5, including the reticulated foam felt material 7 which possesses properties useful for adhesive application. The foam felt 7 has two purposes. Firstly to absorb and transmit (i.e. "wick") adhesive released from the ampoule, and secondly as to dispense adhesive onto a substrate surface directly (such as onto wounded skin to assist in wound closure). The foam felt 7 provides an effective surface for such application of adhesive, and may simply be drawn over the target substrate to cause adhesive to be applied thereon.

As clearly seen in FIG. 5, the reticulated foam felt is in an angled configuration providing two generally planar applicator surfaces 7a and 7b at an acute angle relative to each other and connected by a radiussed applicator surface 7c. This shape allows for both and broad application dependent on orientation. A commercially available material suitable for use as the foam felt 7 is SIF Felt® Grade [e.g. 3-900Z SIF com 3]. The foam felt 7 may, for example, have a thickness of 3 mm.

The structure of the applicator 1 is described in more detail below.

The receiver 3 of the applicator 1 comprises a cylindrical body of plastics material and having a cylindrical wall 11, a closed first end 13 and an open second end 15. The ampoule of adhesive is accommodated in the hollow of the receiver cylindrical body. The cylindrical wall 11 of the cylindrical body is comprised of deformable material which may be so-deformed to cause the ampoule within to be fractured and to release adhesive. Upon fracture of the ampoule, the adhesive is able to flow towards the open end 15 of the cylindrical body and on towards the applicator tip 5 for application there from by means of reticulated foam felt 7.

Figure 2:
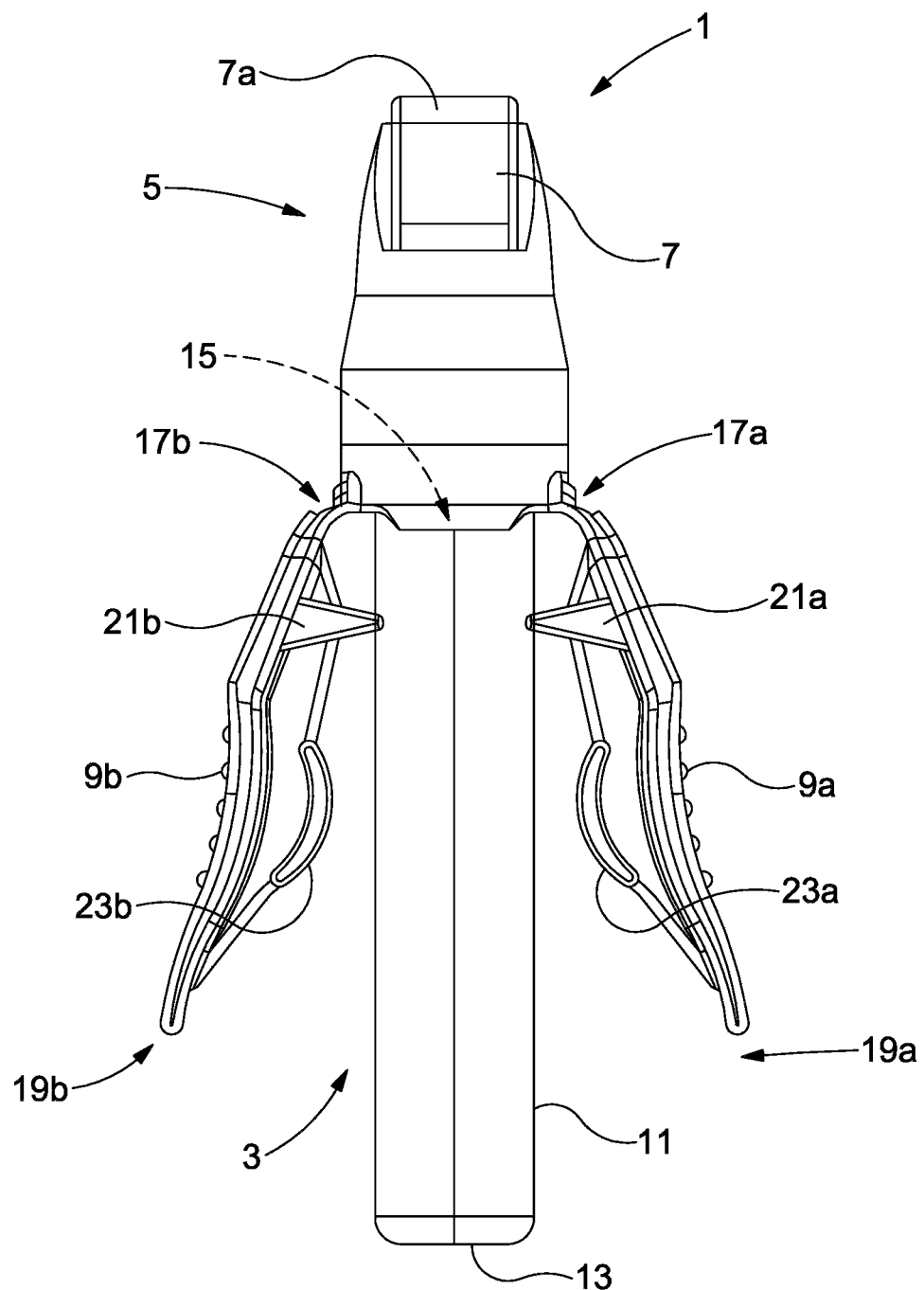
FIG. 2 is a schematic top-down view of the adhesive applicator depicted in FIG. 1.
Figure 3:
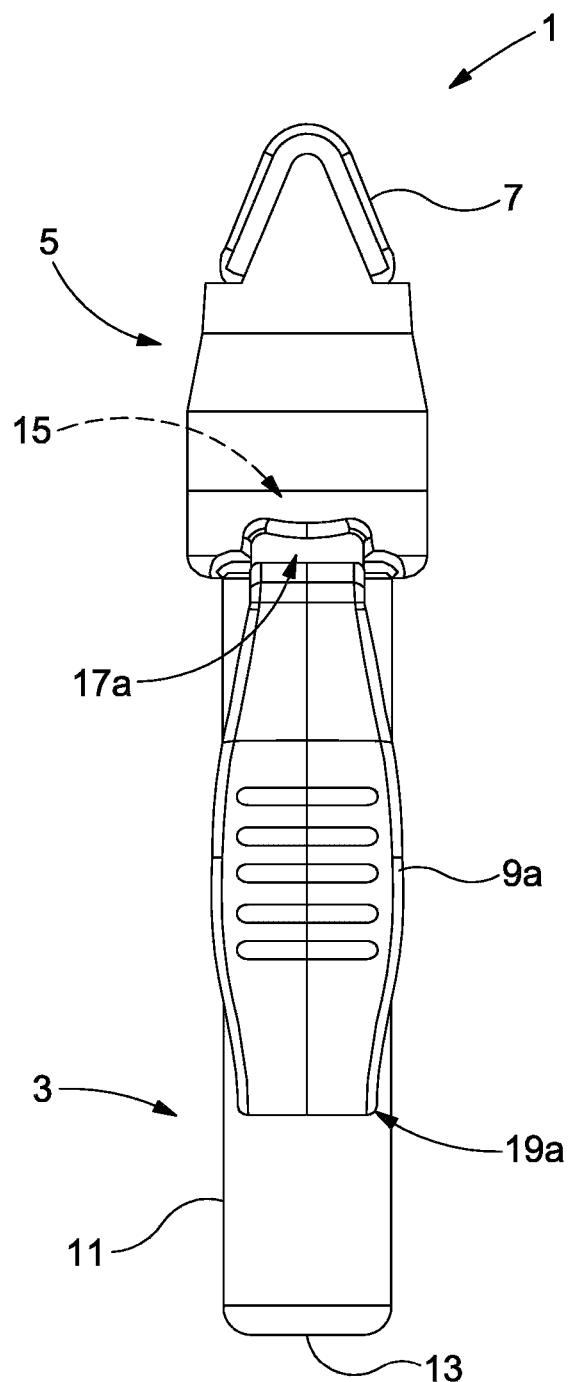
FIG. 3 is a schematic side view of the adhesive applicator depicted in FIG. 1.

The pair of wings 9a, 9b is provided on the cylindrical body of the receiver 3 to assist expression of adhesive as described more fully below. The two wings 9a, 9b are diametrically opposed across the cylindrical body as best understood with reference to FIG. 2. Each wing 9a, 9b in the pair has a first, inside end portion 17a, 17b and a second, outside end portion 19a, 19b. The two inside end portions 17a, 17b of the wings 9a, 9b are affixed to the receiver 3 at a position adjacent to the receiver open end 15. The outside ends 19a, 19b of the wings 9a, 9b are splayed out away from the cylindrical wall 11 but are movable toward the cylindrical wall 11 when a user applies opposing ("squeezing-together") finger pressure to the outside ends 19a, 19b to apply pressure to the cylindrical body of the receiver 3.

Each of the wings 9a, 9b and has a generally triangular pressure barb 21a, 21b provided thereon, each respectively projecting "inwards" toward the cylindrical wall 11 of the receiver 3. The pressure barbs 21a, 21b bear upon the cylindrical wall 11 of the receiver 3 in an area proximate to its open end 15. When the user applies a squeezing-together pressure to the two wings 9a, 9b, the barbs 21a, 21b cause the pressure to be focused as a compressing force on the cylindrical wall 11. This compressing force distorts the wall 11 of the cylindrical body of the receiver 3 and causes the pressure to be applied as an ampoule-fracturing force upon the ampoule accommodated within receiver 3. Fracture of the ampoule causes adhesive contained within to be released for application.

Each of the wings 9a, 9b additionally includes a pressure pad 23a, 23b, each pad respectively projecting "inwards" toward the cylindrical wall 11 of the receiver 3. Application of pressure to the wings 9a, 9b causes these pads 23a, 23b to bear upon the cylindrical wall 11 of the receiver 3, thereby applying a wall-distorting force to the wall 11 and thus applying pressure on the now-fractured ampoule. Application of such force assists expression of adhesive out of the ampoule through the fracture. Released adhesive expressed from the ampoule flows towards the open end 15 of the cylindrical body of the receiver 3 towards and into the applicator tip 5.

As best shown in FIG. 4, the applicator tip comprises a hollow former 25 mounted on the open end 15 of the tubular body of the receiver 3. The former 25 has an openwork end face 27 remote from the body of the receiver 3 which is inclined to the longitudinal axis of the former 25. The openwork end face 27 is in the form of a mesh for inhibiting shards of the ampoule, once fractured, from contacting the foam felt material 7, the apertures in the mesh being sized do not have any dimension larger than 0.5 mm so as to inhibit passage of shards large enough to cause injury.

The reticulated foam felt 7 is supported over the inclined end face 27 of the former 25 to form a correspondingly inclined application surface external of the applicator 1. The foam felt 7 absorbs and transmits adhesive released from the ampoule and passing through the mesh, and is used to dispense adhesive onto a substrate surface directly. The shaping of the foam felt material 7, as dictated by the inclined face of the former 25 on which it is supported, provides an effective surface for application of the adhesive, which may simply be wiped over the target substrate to cause adhesive to be applied thereon.

The former 25 has first and second planar sides 29a, 29b which are opposed to each other and which extend over different lengths away from the tubular body of the receiver 3. The former 25 further comprises third and fourth planar sides 29c, 29d (the fourth side not being visible in the drawings), that are opposed to each other and normal to the first and second planar sides 29a, 29b. The foam felt material 7 is located over the end face 27 and the first and second sides 29a, 29b.

The reticulated foam felt 7 is held in position by a collar 31 locating around the base of the former 25. The collar 31 has two opposed lugs 33a, 33b projecting therefrom, each configured to locate over a respective one of the third and fourth planar sides 29c, 29d of the former 25.

The former 7 and the collar 31 are each provided with cooperating formations to hold the collar 31 in place on the former 7. The third and fourth planar sides 29c, 29d are provided with a raised formation 35 formed with a ridge 37 extending transverse to the axis of the tubular body of the receiver 3. Each of the lugs 33a, 33b is formed on its inner surface with a recess 39 (only one being shown in FIG. 4) complementary to said raised formation 35 and formed with a groove 41 complementary to said ridge 37.

Collar 31 is located in position by pressing it downwardly (as viewed in FIG. 4) over the reticulated foam felt so that ridges 37 locate in grooves 41. As a result, reticulated foam felt 7 is firmly located between former 25 and collar 31, accidental axial removal of the latter being prevented by virtue of the engagement of ridges 37 in grooves 31. Additionally, rotation of the collar 31 is prevented by location of raised portions 35 in recesses 39.

The invention claimed is:

1. An adhesive applicator comprising
   a receiver having a tubular body with a closed first end and an opposed second end, said tubular body having a deformable wall,
   an adhesive composition contained within the tubular body, and
   an applicator tip mounted on the tubular body and comprising a foam material having an applicator surface external of the applicator for applying said adhesive, the applicator being such that deformation of the tubular body causes said adhesive to be expressed through the applicator tip,
   wherein the foam material is a reticulated foam felt and the second end is an open end;
   the applicator tip comprises a hollow former, mounted on the open end of the tubular body, having an openwork end face remote from the body and inclined to the longitudinal axis thereof, said openwork end face being a shard barrier configured in the form of a mesh between the tubular body and the reticulated foam felt; and
   said reticulated foam felt being supported over the end face of the hollow former.

2. The applicator of claim 1 wherein the reticulated foam felt material is comprised of polyurethane.

3. The applicator of claim 1 wherein the foam felt material has a firmness grade of about 2 to 4.

4. The applicator of claim 3 wherein the foam felt material has a firmness grade of about 3.

5. The applicator of any one of claim 1 wherein the adhesive composition is contained within a sealed ampoule formed of a frangible material such that deformation of the wall fractures the ampoule to release the adhesive composition contained therein and express the adhesive composition through the applicator tip.

6. The applicator of claim 1 wherein the mesh has apertures preventing passage through the mesh of a shard having a dimension greater than 0.5 mm.

7. The applicator of claim 1 wherein the former has first and second planar sides which are opposed to each other and which extend over different lengths away from the tubular body, and further comprises third and fourth planar sides that are opposed to each other, and wherein said foam felt material is located over said end face and at least partly over the first and second sides.

8. The applicator of claim 7 wherein the first, second, third and fourth planar sides are impermeable to adhesive.

9. The applicator of claim 7 wherein the reticulated foam felt is held in position by a collar locating around the base of the former and having two opposed lugs projecting therefrom, each configured to locate over a respective one of the third and fourth planar sides of the former body, said third and fourth planar sides and said lugs having co-operating formations to locate the collar in position.

10. The applicator of claim 9 wherein each of the third and fourth sides are provided with a raised formation formed with a ridge extending transverse to the axis of the tubular body, and each of said lugs is formed on its inner surface with a recess complementary to said raised formation and formed with a groove complementary to said ridge.

11. The applicator of claim 1 wherein a plug is located in the second end of the tubular body to retain the adhesive composition therein and wherein the plug is moveable away from the first end on deformation of the tubular body to allow adhesive to be released from the tubular body and expressed through the applicator tip.

12. The applicator of claim 1 further comprising a pair of wings positioned diametrically across the tubular body, each wing being affixed at one end to the receiver, with the other end being splayed out away from the tubular wall but being movable toward the tubular wall when a user applies opposing finger pressure to the splayed ends;

wherein each of the wings has a pressure barb facing toward and bearing upon the tubular wall, through which an ampoule-fracturing force may be applied to the tubular wall upon movement of the wings.

13. The applicator of claim 12 wherein each of the wings additionally comprises a pressure pad facing toward the tubular wall, through which pressure pad a compressing force may be applied to the tubular wall for expressing adhesive through the second end of the tubular body.

14. The applicator of claim 1, wherein the adhesive composition comprises a polymerisable cyanoacrylate ester adhesive which, in monomeric form, is represented by the following formula:

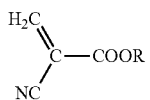

where R is selected from: alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula II:

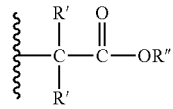

wherein each R' is independently selected from: hydrogen and methyl, and R" is selected from: alkyl of from 1 to 6 carbon atoms, alkenyl of from 2 to 6 carbon atoms, alkynyl of from 2 to 6 carbon atoms, cycloalkyl of from 3 to 8 carbon atoms, aralkyl selected from benzyl, methylbenzyl and phenylethyl, phenyl, and phenyl substituted with 1 to 3 substituents selected from hydroxy, chloro, bromo, nitro, of alkyl 1 to 4 carbon atoms, and alkoxy of from 1 to 4 carbon atoms.

15. The applicator of claim 14, wherein the polymerisable cyanoacrylate ester is 1-methylheptyl cyanoacrylate.

16. The applicator of claim 14, wherein the adhesive composition include, at least one of an accelerator, rheology modifier and an antimicrobial agent.

* * * * *